United States Patent [19]

Mori et al.

[11] Patent Number: 5,583,271
[45] Date of Patent: Dec. 10, 1996

[54] METHOD FOR CONTINUOUSLY PRODUCING ALKADIENOLS

[75] Inventors: Tomoyuki Mori; Hiroshi Kameo; Shinji Isogai; Soichiro Saita, all of Kurashiki, Japan

[73] Assignee: Mitsubishi Chemical Corporation, Tokyo, Japan

[21] Appl. No.: 576,599

[22] Filed: Dec. 21, 1995

[30] Foreign Application Priority Data

Dec. 26, 1994 [JP] Japan .................................. 6-337197
Feb. 6, 1995 [JP] Japan .................................. 7-018129

[51] Int. Cl.$^6$ .......................... C07C 29/04; C07C 29/36; C07C 33/035
[52] U.S. Cl. ........................................ 568/909.5
[58] Field of Search ............................... 568/909.5

[56] References Cited

U.S. PATENT DOCUMENTS

| | | | |
|---|---|---|---|
| 3,670,032 | 6/1972 | Romanelli | 568/909.5 |
| 4,990,698 | 2/1991 | Wada et al. | 568/909.5 |
| 5,169,981 | 12/1992 | Packett | 568/909.5 |
| 5,302,750 | 4/1994 | Livingston | 568/909.5 |
| 5,481,049 | 1/1996 | Sato et al. | 568/909.5 |

FOREIGN PATENT DOCUMENTS

| | | |
|---|---|---|
| 1-25739 | 1/1989 | Japan . |
| 1-25738 | 1/1989 | Japan . |
| 1-85988 | 3/1989 | Japan . |
| 2-172924 | 7/1990 | Japan . |
| 3-232831 | 10/1991 | Japan . |

*Primary Examiner*—Joseph E. Evans
*Attorney, Agent, or Firm*—Oblon, Spivak, McClelland, Maier & Neustadt, P.C.

[57] ABSTRACT

A method for continuously producing alkadienols, which comprises subjecting a conjugated alkadiene and water to a hydration dimerization reaction in a continuous type reactor in the presence of carbon dioxide and a catalyst comprising a palladium compound and a phosphorus compound, wherein a hydrophobic phosphorus compound is used as the phosphorus compound, and the reaction is carried out in the presence of an amine while maintaining the concentration of the conjugated alkadiene in the reaction solution in the reactor within a range of from 0.5 to 4.5 wt %.

16 Claims, 1 Drawing Sheet

METHOD FOR CONTINUOUSLY
PRODUCING ALKADIENOLS

BACKGROUND OF THE INVENTION

1. Field of the Invention

The present invention relates to a method for continuously producing alkadienols. More particularly, it relates to an industrially advantageous method for continuously producing alkadienols.

DISCUSSION OF BACKGROUND

Alkadienols, particularly octadienols including octa-2,7-diene-1-ol are industrially important compounds as intermediates for producing n-octanol or its esters.

Heretofore, as a method for producing alkadienols, a method is known wherein a conjugated alkadiene and water are subjected to a dimerization reaction in the presence of carbon dioxide and a catalyst comprising a palladium compound and a phosphorus compound. For example, Japanese Examined Patent Publication No. 10565/1975 discloses a dimerization reaction wherein a triphenylphosphine is used as a ligand of the palladium compound. However, the yield of alkadienols is inadequate, and, for example, dialkadienyl ethers and alkatrienes are produced as by-products.

As a method for improving the selectivity for an alkadienol (such as octa-2,7-diene-1-ol), Japanese Examined Patent Publication No. 67129/1993 proposes a method wherein by using a catalyst comprising palladium and a hydrophilic phosphorus compound, the reaction is continuously carried out in the presence or absence of an amine while maintaining the molar ratio of the starting material conjugated alkadiene (such as 1,3-butadiene) to the product alkadienol at a level of at least 0.6. Namely, this publication indicates that the alkadienol can be obtained with high selectivity when the conversion of the conjugated alkadiene is lowered while maintaining the conjugated alkadiene concentration in the reaction solution at a high level. In other words, it indicates that the selectivity of the alkadienol decreases if the conversion is increased to a level of e.g. at least 70% while maintaining the concentration of the conjugated alkadiene in the reaction solution at a low level. In short, it suggests that good selectivity and conversion are in an antinomic relation to each other and are difficult to attain.

However, the conversion of the conjugated alkadiene being low, means that the production efficiency is low, and as such, is not necessarily industrially advantageous. Further, to maintain the concentration of the conjugated alkadiene in the reaction solution at a high level, a compressor of a large size is required for recycling an unreacted conjugated alkadiene discharged from the reaction solution to the reactor, and such a large size compressor is not only expensive but requires a high operational power cost, such being disadvantageous from the industrial point of view.

SUMMARY OF THE INVENTION

Under these circumstances, it is an object of the present invention to provide an industrially advantageous method for continuously producing alkadienols, whereby the selectivity and the conversion can be improved without increasing the concentration of the conjugated alkadiene in the reaction solution.

As a result of extensive studies to accomplish the above object, the present inventors have found that it is surprisingly possible to increase the selectivity for alkadienols while maintaining a high conversion of the conjugated alkadiene at a low concentration of the conjugated alkadiene in the reactor, if the reaction is carried out in the presence of an amine using a hydrophobic phosphorus compound as a catalyst component under such a high conversion condition as heretofore believed to be impossible to attain high selectivity.

The present invention has been accomplished on the basis of the above discovery and provides a method for continuously producing alkadienols, which comprises subjecting a conjugated alkadiene and water to a hydration dimerization reaction in a continuous type reactor in the presence of carbon dioxide and a catalyst comprising a palladium compound and a phosphorus compound, wherein a hydrophobic phosphorus compound is used as the phosphorus compound, and the reaction is carried out in the presence of an amine while maintaining the concentration of the conjugated alkadiene in the reaction solution in the reactor within a range of from 0.5 to 4.5 wt %.

DETAILED DESCRIPTION OF THE PREFERRED EMBODIMENTS

Figure 1:
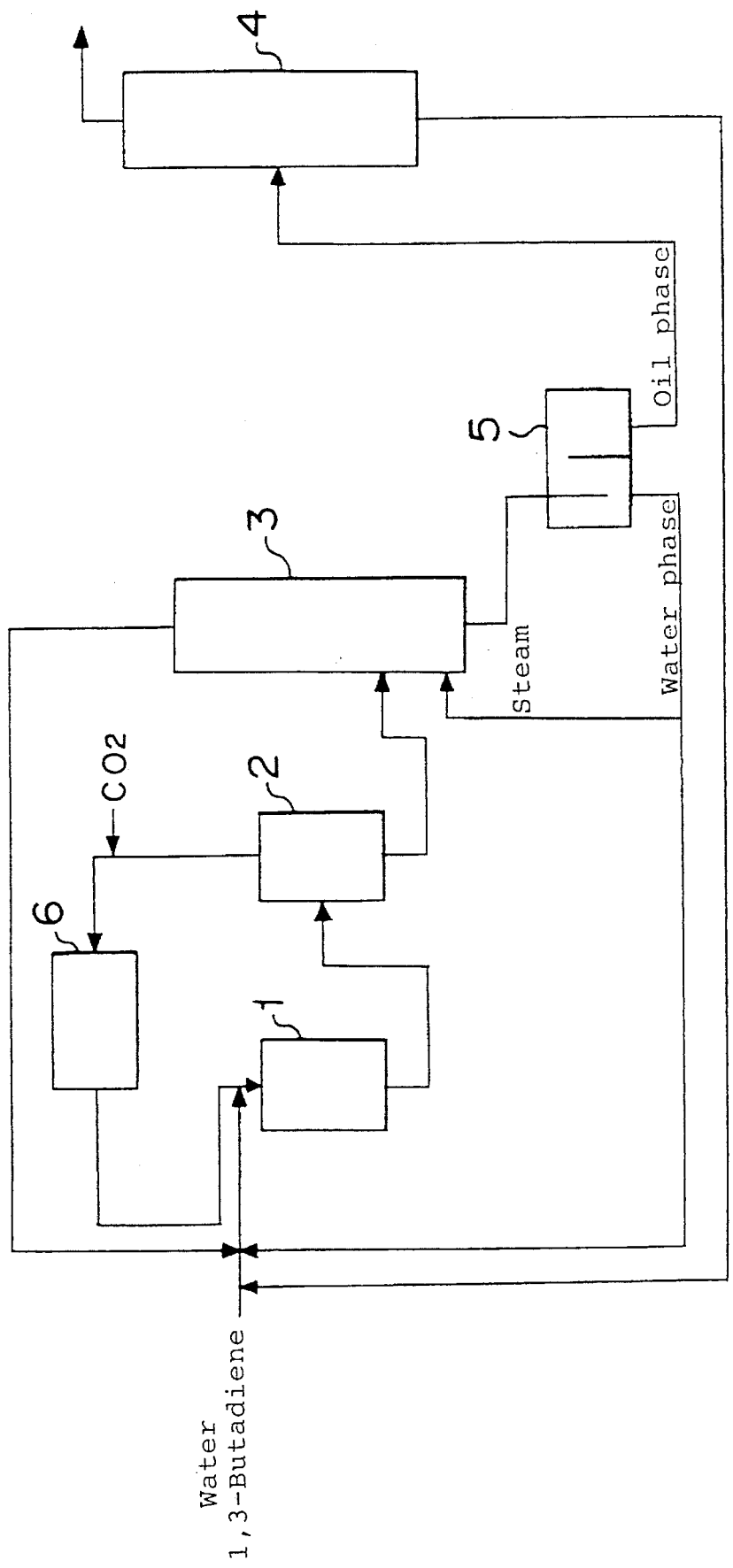
FIG. 1 is a flow chart showing the construction of the apparatus for reaction used in Examples 3 and 4 and Comparative Example 4.

Now, the present invention will be described in detail.

The starting material conjugated alkadiene may, for example, be 1,3-butadiene, 2-ethyl-1,3-butadiene, 2,3-dimethl-1,3-butadiene, isoprene, 1,3-pentadiene, chloroprene or 1,3-octadiene. And, as a readily available 1,3-butadiene starting material, so-called BBP (butane-butadiene product), i.e. the $C_4$ fraction mixture in the naphtha decomposition product, may be mentioned in addition to purified 1,3-butadiene.

When BBP is used as the starting material, it is preferred that acetylenes and arenes contained in the BBP starting material are preliminarily decomposed and removed. The total concentration of acetylenes and arenes in the 1,3-butadiene starting material (BBP) is desired to be as low as possible and is usually not higher than about 1.0 wt % relative to 1,3-butadiene. A method for reducing acetylenes and arenes is not particularly limited, and a conventional method may suitably be employed.

The water as another starting material, may be water having a purity to such an extent not to give an influence over the hydration dimerization reaction.

The form and the valency of the palladium compound to be used as the catalyst in the present invention are not particularly limited. The palladium compound may, for example, be a metal palladium such as palladium black or palladium metal supported on a carrier; a zerovalent palladium complex such as bis(t-butylisonitrile)palladium (0), bis(t-amylisonitrile)palladium (0), bis(cyclohexylisonitrile)palladium (0), bis(phenylisonitrile)palladium (0), bis(p-toluylisonitrile)palladium (0), bis(2,6-dimethylphenylisonitrile)palladium (0), tris(dibenzylideneacetone)dipalladium (0), (1,5-cyclooctadiene)(maleic anhydride)palladium (0), bis(norbornene)(maleic anhydride)palladium (0), bis(maleic anhydride)(norbornene)palladium (0), (dibenzylideneacetone)(bipyridyl)palladium (0), or (p-benzoquinone)(o-phenanthroline)palladium (0); a tetrakis(phosphine)palladium, tris(phosphine)palladium or bis(phosphine)palladium complex having a phosphine compound as a ligand, such as tetrakis(triphenylphosphine)palladium (0), tris(triphenylphosphine)palladium (0), bis(tritolylphosphine)palladium (0), bis(trixylyl)palladium (0), bis(trimethylphosphine)palladium (0), bis(tritetramethylphenyl)palladium (0) or bis(trimethylmethoxyphenylphosphine)palladium (0), or the corresponding tetrakis(phosphite)palladium, tris(phosphite)palladium or bis(phosphite)palladium complex having a phosphite compound as a ligand; an inorganic acid salt of palladium such as palladium (II) chloride, palladium (II) nitrate, tetraaminedichloropalladium (II) or disodiumtetrachloropalladium (II); a palladium carboxylate such as palladium (II) acetate, palladium (II) benzoate or palladium (II) α-picolate; a chelate compound of palladium such as bis(acetylacetone)palladium (II) or bis(8-oxyquinoline)palladium (II); or a bivalent palladium complex such as bis-(allyl)palladium (II), (η-allyl)(η-cyclopentadienyl)palladium (II), (η-cyclopentadienyl)(1,5-cyclooctadiene)palladium (II) tetrafluoroborate, bis(benzonitrile)palladium (II) acetate, di-μ-chlorodichlorobis(triphenylphosphine)dipalladium (II), bis(tri-n-butylphosphine)palladium (II) acetate or 2,2-bipyridylpalladium (II) acetate.

Among the above palladium compounds, tetrakis(triphenylphosphine)palladium (0), bis(tritolylphosphine)palladium (0), bis(trixylyl)palladium (0), bis(trimethylmethoxyphenylphosphine)palladium (0), palladium (II) acetate or bis(acetylacetone)palladium (II) is preferred.

In the present invention, it is necessary to use a hydrophobic phosphorus compound as a cocatalyst. As the hydrophobic phosphorus compound, various phosphines, phosphinites, phosphonites and phosphites may be mentioned. Specific examples thereof include a trialkylphosphine such as trioctylphosphine, tributylphosphine or dimethyloctylphosphine; a tricycloalkylphosphine such as tricyclohexylphosphine; a triarylphosphine such as triphenylphosphine, tritolylphosphine, trixylylphosphine, trimesitylphosphine, tris(tetramethylphenyl)phosphine, diphenyl-p-chlorophenylphosphine or tris(p-methoxyphenyl)phosphine; a tertiary alkylarylphosphine such as diphenylethylphosphine, dimethylphenylphosphine, bis(diphenylphosphine)methane or 1,2-bis(diphenylphosphine)ethane; an alkylphosphinite such as dioctyloctoxyphosphine or dibutylbutoxyphosphine; an arylphosphinite such as diphenylphenoxyphosphine, ditolyltolyloxyphosphine or dixylylxylyloxyphosphine; an alkylarylphosphinite such as diphenylethoxyphosphine or diethylphenoxyphosphine; an alkylphosphonite such as octyldioctoxyphosphine or butylbutoxyphosphine; an arylphosphonite such as phenyldiphenoxyphosphine, tolylditolyloxyphosphine or xylyldixylyloxyphosphine; an alkylarylphosphonite such as phenyldiethoxyphosphine or ethyldiphenoxyphosphine; a trialkylphosphite such as trioctylphosphite, tributylphosphite or dimethyloctylphosphite; a tricycloalkylphosphite such as tricyclohexylphosphite; a triarylphosphite such as triphenylphosphite, tritolylphosphite or trixylylphosphite; and an alkylarylphosphite such as diphenylethylphosphite or dimethylphenylphosphite.

Among the above hydrophobic phosphorus compounds, a phosphine or phosphite having at least 19 carbon atoms is preferred from the viewpoint of the selectivity for alkadienols. Specifically, tritolylphosphine, trixylylphosphine, trimesitylphosphine or tris(tetramethylphenyl)phosphine is, for example, preferred.

The carbon dioxide may be in any form when it is supplied, so long as it is present in the form of carbon dioxide in the reaction system. For example, in addition to molecular carbon dioxide, carbonic acid, a carbonate or a hydrogen carbonate or an adduct of carbon dioxide or carbonic acid with an amine, may be mentioned.

In the present invention, it is important to carry out the reaction in the presence of an amine. By the presence of the amine, formation of carbon anions is promoted, whereby the reaction rate is remarkably improved, and formation of high boiling by-products will be suppressed. As such an amine, a tertiary amine is preferably employed.

Specific examples of the tertiary amine include a trialkyl amine such as trimethylamine, triethylamine, tripropylamine, tributylamine, trioctylamine or tridecylamine; and an alkanol amine such as triethanolamine or tripropanolamine; an aromatic amine such as dimethylaniline, triphenylamine or tribenzylamine; N-methylpyrrolidine, N-methylpiperidine, N-methylmorpholine, N,N'-dimethylpiperazine, N-methylpipecoline, N,N,N',N'-tetramethyl-1,3-butane diamine, and N,N,N'N'-tetramethylhexamethylene diamine. Among them, a trialkylamine such as triethylamine or trioctylamine is preferred.

In the present invention, it is preferred to use a solvent in order to carry out the reaction smoothly. As the solvent for the reaction, any solvent may be employed which is capable of dissolving at least partially the conjugated alkadiene, the palladium compound and the phosphorus compound.

Examples of the solvent for reaction include ethers such as diethyl ether, dioxane, tetrahydrofuran, ethylene glycol dimethyl ether and tetraethylene glycol dimethyl ether; ketones such as acetone, methyl ethyl ketone, diethyl ketone, methyl isopropyl ketone and ethyl n-butyl ketone; nitriles such as acetonitrile, propionitrile and benzonitrile; aromatic hydrocarbons such as benzene, toluene, xylene and ethylbenzene; alkanes such as pentane, hexane and heptane; alkenes such as hexene or octene; sulfoxides such as dimethylsulfoxide; sulfones such as sulfolane; nitro compounds such as nitrobenzene and nitromethane; pyridine derivatives such as pyridine and α-pyrroline; amines such as triethylamine; amides such as acetamide, propionamide, N,N-dimethylformamide, N,N-dimethylacetamide and N,N-diethylacetamide; alcohols such as methanol, ethanol, n-propanol, isopropanol, nbutanol, isobutanol, t-butanol and n-octanol; and carboxylic acids such as formic acid, acetic acid, propionic acid and butyric acid. These solvents may be used alone or in combination as a solvent mixture.

In the present invention, alkadienols are continuously produced by using a continuous type reactor and by subjecting the conjugated alkadiene and water to a hydration dimerization reaction in the presence of an amine, carbon dioxide and a catalyst comprising the palladium compound and the hydrophobic phosphorus compound. Here, it is important to carry out the above continuous reaction while maintaining the concentration of the conjugated alkadiene in the reaction solution in the reactor within a range of from 0.5 to 4.5 wt %.

It is totally unexpected from the teaching disclosed in Japanese Examined Patent Publication No. 67129/1993 that high selectivity and high conversion can be attained at a concentration of the conjugated alkadiene in the reaction solution within a range of from 0.5 to 4.5 wt %. According to the present invention, the amount of an unreacted conjugated alkadiene discharged from the reaction solution is small, and the compressor for recycling the unreacted conjugated alkadiene to the reactor may be of a small size. The concentration of the conjugated alkadiene in the reaction solution is selected preferably within a range of from 0.5 to 4.0 wt %, more preferably from 1.0 to 3.5 wt %, most preferably from 2 to 3 wt %.

The amount of the palladium compound is selected usually within a range of from 0.00001 to 1 mol, preferably from 0.0001 to 0.5 mol, as the amount of palladium atoms per mol of the conjugated alkadiene. If the amount of the palladium compound is small, the reaction rate is low and the reactor tends to be of a large size. On the other hand, if the amount is too much, the palladium compound is likely to precipitate, whereby handling of the catalyst tends to be inconvenient.

The amount of the hydrophobic phosphorus compound is selected usually within a range of from 0.1 to 100 mols, preferably from 1 to 50 mols, per mol of palladium.

The upper limit of the amount of carbon dioxide is determined simply by economical reasons, and use of an excess amount will not adversely affect the reaction. Carbon dioxide is used usually in amount of at least one mol, preferably at least 10 mols, per mol of palladium.

The amount of the amine is selected usually within a range of from 0.01 to 20 wt %, preferably from 0.1 to 15 wt %, more preferably from 0.01 to 10 wt %, as the concentration in the reactor.

Under the reaction conditions in the present invention, the addition reaction of water constitutes a rate-limiting step. Accordingly, the higher the molar ratio of the water/the conjugated alkadiene, the better. The molar ratio of the water/the conjugated alkadiene is preferably at least 4, more preferably at least 5, most preferably at least 7. If the molar ratio of the water/the conjugated alkadiene is low, the addition reaction of water tends to be slow, whereby by-products are likely to form, and the selectivity will be low. The concentration of water in the reactor is preferably from 1 to 20 wt %, more preferably from 3 to 15 wt %, most preferably from 4 to 12 wt %. If the concentration of water in the reactor is too high, phase separation will take place in the reactor, and the selectivity for alkadienols tends to be low.

In the present invention, it is advantageous to conduct the reaction under such a condition that the conversion of the conjugated alkadiene would be at least 75%. Even under such a high conversion condition, high selectivity can be accomplished as shown by the Examples given hereinafter. A preferred value of the conversion of the conjugated alkadiene is at least 80%

The reaction temperature can be selected within a wide range of from room temperature to about 180° C., but it is preferably within a range of from 50° to 130° C., more preferably from 60° to 100° C.

Further, the reaction pressure may be selected within a wide range of from atmospheric pressure to about 200 kg/cm$^2$, but it is preferably from 3 to 70 kg/cm$^2$.

The residence time is usually at most 10 hours, preferably from 0.1 to 8 hours, more preferably from 0.3 to 5 hours, most preferably from 0.35 to 3 hours. If the reaction time is too short, the amount of formation of the alkadienols tends to be small, and if it is too long, there will be a drawback such that palladium will be metallized.

At the time of the reaction, an inert gas such as nitrogen, helium or argon may be present in the reaction system, as disclosed in Japanese Examined Patent Patent Publication No. 10565/1975.

The reaction solution contains an unreacted conjugated alkadiene, the catalyst, water, a solvent, etc. in addition to alkadienols as the main products, and alkatrienes, dialkadienyl ethers, organic carboxylic acids and esters, as by-products. When the conjugated alkadiene is 1,3-butadiene, the main product will be octa-2,7-diene-1-ol, and by-products will be octa-1,7-diene-3-ol, octatrienes, dioctadienyl ethers and organic carboxylic acids. The amounts of such reaction byproducts formed, vary depending upon the reaction conditions. However, they are usually respectively within a few mol %, based on the conjugated alkadiene. Therefore, the alkadienols as the main product will be recovered from the reaction solution by a separating means such as distillation.

Further, in the present invention, alkadienols are continuously produced by recovering the product from the reaction solution containing the catalyst withdrawn from the reactor and recycling at least a part of the catalyst solution to the reactor, whereby the reaction is carried out while maintaining the amount of high boiling by-products, the conjugated alkadiene and the alkadienols in the reaction solution in the reactor under certain specific conditions. Here, the high boiling by-products mean products having higher boiling points than the alkadienols as the products and include, for example, dialkadienyl ethers and organic carboxylic acids. When the conjugated alkadiene is 1,3-butadiene, the high boiling by-products will be dioctadienyl ethers, organic carboxylic acids, etc.

Specifically, the ratio of the weight of the high boiling by-products to the total weight of the conjugated alkadiene and the alkadienols present invention reaction solution in the reactor (hereinafter referred to as the weight ratio of high boiling products) is maintained preferably within a range of from 0.1 to 2.0, more preferably from 0.15 to 1.2, still more preferably from 0.2 to 1.0, most preferably from 0.25 to 0.85. The concentration of the high boiling by-products in the reaction solution is not particularly restricted so long as the weight ratio of the high boiling products satisfies the above range. However, it is preferably maintained within a range of from 3 to 25 wt %, more preferably from 5 to 20 wt %, most preferably from 7 to 15 wt %.

Further, with respect to alkadienols at the time of calculating the above weight ratio of high boiling products, for example, in a case where 1,3-butadiene is used as the starting material, the weights of all octadienols formed as isomers will be taken into account. The concentration of the high boiling by-products in the reaction solution can be adjusted by returning a part of the high boiling by-products from the reaction solution to the reactor after separating them by a conventional method such as purging, distillation, extraction or crystallization.

Now, the present invention will be described in further detail with reference to Examples. However, it should be understood that the present invention is by no means restricted to such specific Examples.

EXAMPLE 1

Into a 200 ml stainless steel autoclave equipped with an electromagnetic induction stirrer, palladium acetate, tris(2,5-xylyl)phosphine, triethylamine, water, 1,3-butadiene and an acetone solvent were continuously supplied, and the internal pressure of the autoclave was maintained at a level of 20 kg/cm$^2$G by carbon dioxide.

While maintaining the temperature at a level of 75° C., the amount of liquid at a level of 150 ml and the residence time at a level of 1.9 hours in the autoclave, the reaction solution at the liquid phase portion in the autoclave was continuously withdrawn, and the respective components were analyzed, whereby 1,3-butadiene: 2.8 wt %, water: 5.4 wt %, palladium: 179 wt ppm, tris(2,5-xylyl)phosphine: 5.4 wt %, triethylamine: 10 wt %, 1-hydroxy-2,7-octadiene: 15.3 wt %, 3hydroxy-1,7-octadiene: 0.74 wt %, by-products: 1.1 wt %.

Based on the concentration (17.6 wt %) of 1,3-butadiene in the total feed supplied to the autoclave, the conversion of 1,3-butadiene and the selectivity, based on 1,3-butadiene, for the total of 1-hydroxy-2,7-octadiene and 3-hydroxy-1,7-octadiene were determined, whereby they were 84.1% and 93%, respectively.

EXAMPLE 2

A continuous reaction was carried out in the same manner as in Example 1 except that in Example 1, tris(2,5-xylyl)phosphine was changed to tri(otolyl)phosphine, and the residence time was changed to 1.3 hours. The reaction solution at the liquid phase portion in the autoclave was continuously withdrawn, and the respective components were analyzed, whereby 1,3-butadiene: 2.4 wt %, water: 5.4 wt %, palladium: 270 wt ppm, tri(o-tolyl)phosphine: 2.0 wt %, triethylamine: 10 wt %, 1-hydroxy-2,7-octadiene: 18.4 wt %, 3-hydroxy-1,7-octadiene: 0.9 wt %, by-products: 1.1 wt %.

Based on the concentration (20wt %) of 1,3-butadiene in the total feed supplied to the autoclave, the conversion of 1,3-butadiene and the selectivity, based on 1,3-butadiene, for the total of 1-hydroxy-2,7-octadiene and 3-hydroxy-1,7-octadiene, were determined, whereby they were 88% and 94%, respectively.

COMPARATIVE EXAMPLE 1

A continuous reaction was carried out in the same manner as in Example 1 except that in Example 1, the residence time was changed to 0.94 hours. The reaction solution at the liquid phase portion in the autoclave was continuous withdrawn, and the respective components were analyzed, whereby 1,3-butadiene: 5.8 wt %, water: 6.7 wt %, palladium: 182 wt ppm, tris(2,5-xylyl)phosphine: 0.9 wt %, triethylamine: 10 wt %, 1-hydroxy-2,7-octadiene: 12.8 wt %, 3-hydroxy-1,7-octadiene: 0.6 wt %, by-products: 1.2 wt %.

Based on the concentration (18.4 wt %) of 1,3-butadiene in the total feed supplied to the autoclave, the conversion of 1,3-butadiene and the selectivity, based on 1,3-butadiene, for the total of 1-hydroxy-2,7 -octadiene and 3-hydroxy-1,7-octadiene, were determined, whereby they were 68.5% and 91%, respectively.

COMPARATIVE EXAMPLE 2

A continuous reaction was carried out in the same manner as in Example 1except that in Example 1, tris(2,5-xylyl)phosphine was changed to tri(otolyl)phosphine, and the residence time was changed to 1.0 hour. The reaction solution at the liquid phase portion in the autoclave was continuously withdrawn, and the respective components were analyzed, whereby 1,3-butadiene: 5.0 wt %, water: 6.0 wt %, palladium: 195 wt ppm, tri(o-tolyl)phosphine: 1.2 wt %, triethylamine: 10 wt %, 1-hydroxy-2,7-octadiene: 15.1 wt %, 3-hydroxy-1,7-octadiene: 0.64 wt %, by products: 1.6 wt %.

Based on the concentration (20 wt %) of 1,3-butadiene in the total feed supplied to the autoclave, the conversion of 1,3-butadiene and the selectivity, based on 1,3-butadiene, for the total of 1-hydroxy-2,7-octadiene and 3-hydroxy-1,7-octadiene, were determined, whereby they were 75% and 90%, respectively.

COMPARATIVE EXAMPLE 3

A continuous reaction was carried out in the same manner as in Example 1 except that in Example 1, supply of triethylamine was stopped, and the residence time was changed to 3.0 hours. The reaction solution at the liquid phase portion in the autoclave was continuously withdrawn, and the respective components were analyzed, whereby 1,3-butadiene: 2.1 wt %, water: 11.0 wt %, palladium: 729 wt ppm, tris(2,5-xylyl)phosphine: 1.3 wt %, 1-hydroxy-2,7-octadiene: 16.9 wt %, 3-hydroxy-1,7-octadiene: 0.8 wt %, by products: 2.9 wt %.

Based on the concentration (20 wt %) of 1,3-butadiene in the total feed supplied to the autoclave, the conversion of 1,3-butadiene and the selectivity, based on 1,3-butadiene, for the total of 1-hydroxy-2,7-octadiene and 3-hydroxy-1,7-octadiene, were determined, whereby they were 89.5% and 85%, respectively.

EXAMPLE 3

Using the apparatus as shown in FIG. 1, a continuous operation of the reaction of 1,3-butadiene and water was carried out while recycling the catalyst. Upon expiration of 210 hours after initiation of the reaction, the state was as follows.

The reactor 1 was a stainless steel autoclave having an internal capacity of 10 l and equipped with an induction stirrer to which acetone as a recycling solvent (containing triethylamine), a recycling catalyst solution containing high boiling by-products, water and 1,3-butadiene were continuously supplied. The amount of the total feed was 1,181 g/hr. The concentration of 1,3-butadiene and the total concentration of 1-hydroxy-2,7-octadiene and 3-hydroxy-1,7-octadiene in the total feed were 16.7 wt % and 1.9 wt %, respectively. The inner pressure of the autoclave was maintained at 10 kg/cm$^2$G by carbon dioxide, the reaction temperature was 75° C., and the residence time of the reaction solution was 5.6 hours. The composition of the liquid phase portion in the reactor was maintained to be 46.5 wt % of acetone, 9.5 wt % of water, 3.0 wt % of 1,3-butadiene, 16.5 wt % of 1-hydroxy-2,7-octadiene, 0.7 wt % of 3-hydroxy-1,7-octadiene, 10.8 wt % of triethylamine, 7.0 wt % of high boiling by-products, 0.03 wt % of palladium (formed from palladium acetate), and 0.99 wt % of tris(2,5-xylyl)phosphine. Here, the high boiling by-products include dioctadienyl ether, $C_{16}$ unsaturated hydrocarbons, $C_9$ unsaturated carboxylic acids and octadienyl dodecatrienyl ether, etc.

The reaction solution continuously withdrawn from the reactor is supplied to a gas-liquid separator 2, and a liquid separated under 1 kg/cm$^2$G at 25° C. was continuously supplied to a distillation column 3. The distillation column 3 was operated under a column top pressure of 760 mmHg at a reflux ratio of 0.5 with a theoretical plate number of 15 plates, and the reaction solution was supplied to a position corresponding to a theoretical plate number of 13 plates from the top. The solvent acetone and triethylamine distilled from the top of the distillation column 3 were returned to the reactor, while the bottoms were separated into oil and water by an oil-water separator 5. The oil layer was supplied to a distillation column 4. This supplied amount was 323 g/hr. The composition of this oil layer was 60.3 wt % of 1-hydroxy-2,7-octadiene, 2.3 wt % of 3-hydro-1,7-octadiene, 25.3 wt % of high boiling by-products, 0,102 wt % of palladium, and 3.6 wt % of tris(2,5-xylyl)phosphine.

The distillation column 4 was a simple distillation column, which was operated under a pressure of 20 mmHg at an internal temperature at the bottom of 120° C. with a residence time of the bottoms being from 0.3 to 1.3 hours, and the amount of discharge from the bottom was adjusted so that the concentration of the high boiling by-products in the reactor would be 7 wt %. (At the bottom, the high boiling by-products were partially decomposed to low boiling components which would be distilled off, whereby the amount of discharge from the bottom can be adjusted.) The amount of the discharged liquid was 116 g/hr, which contained 70.1 wt % of high boiling by-products, 0.3 wt % of palladium, and 9.8 wt % of tris(2,5-xylyl)phosphine. The discharged liquid containing the high boiling by-products was returned as a recycling catalyst solution to the reactor.

The weight ratio of the high boiling by-products to the conjugated alkadiene (1,3-butadiene) and alkadienols (1-hydroxy-2,7-octadiene and 3-hydroxy-1,7-octadiene) present in the reaction solution in the reactor in this state, was 0.33. The conversion of 1,3-butadiene was 82%, and the selectivity, based on 1,3-butadiene, for the total of 1-hydroxy-2,7-octadiene and 3-hydroxy-1,7-octadiene, was 95.7%.

EXAMPLE 4

Using the same apparatus as used in Example 3, a continuous operation of the reaction of 1,3-butadiene and water was carried out while recycling the catalyst, upon expiration of 304 hours after the initiation of the reaction, the state was as follows.

Into the reactor 1, acetone as a recycling solvent (containing triethylamine), a recycling catalyst solution containing high boiling by-products, water and 1,3-butadiene were continuously supplied. The total amount of the feed supplied was 1,280 g/hr, and the concentration of 1,3-butadiene and the total concentration of 1-hydroxy-2,7-octadiene and 3-hydroxy-1,7-octadiene in the total feed were 8.5 wt % and 2.9 wt %, respectively. The internal pressure of the autoclave was maintained at 10 kg/cm$^2$G by carbon dioxide. The reaction temperature was 75° C., and the residence time of the reaction solution was 4 hours. The composition of the liquid phase portion in the reactor was maintained to be 56.6 wt % of acetone, 7.8 wt % of water, 1.6 wt % of 1,3-butadiene, 10.1 wt % of 1-hydroxy-2,7-octadiene, 0.2 wt % of 3-hydroxyl-1,7-octadiene, 9.6 wt % of triethylamine, 10.1 wt % of high boiling by-products, 0.028 wt % of palladium (formed from palladium acetate) and 0.6 wt % of tris(2,5-xylyl)phosphine. Here, the high boiling by-products included dioctadienyl ether, $C_{16}$ unsaturated hydrocarbons, $C_9$ unsaturated carboxylic acids, octadienyl dodecatrienyl ether, etc.

The composition of the oil layer separated by an oilwater separator 5 was 45 wt % of 1-hydroxy-2,7-octadiene, 0.9 wt % of 3-hydroxy-1,7-octadiene, 45.2 wt % of high boiling by-products, 0.126 wt % of palladium, and 2.7 wt % of tris(2,5-xylyl)phosphine. This oil layer was supplied to a distillation column 4, and the supplied amount was 86 g/hr.

The distillation column 4 was operated under a pressure of 20 mmHg at an internal temperature of the bottom portion of 10° C. with a residence time of the bottoms at the bottom portion was from 0.3 to 1.3 hours, and the amount of the bottoms discharged was adjusted so that the concentration of the high boiling by-products in the reactor would be 10 wt %.

The amount of the discharged bottoms was 157 g/hr, and the bottoms contained 73 wt % of high boiling byproducts, 0.22 wt % of palladium and 5.3 wt % of tris(2,5-xylyl)phosphine. The discharged liquid containing the high boiling by-products was returned as a recycling catalyst solution to the reactor. Other conditions were the same as in Example 3.

The weight ratio of the high boiling by-products to the conjugated alkadiene (1,3-butadiene) and alkadienols (1-hydroxy-2,7-octadiene and 3-hydroxy-1,7-octadiene) present in the reaction solution in the reactor in this state, was 0.85. The conversion of 1,3-butadiene was 81% and the selectivity, based on 1,3-butadiene, for the total of 1-hydroxy-2,7-octadiene and 3-hydroxy-1,7-octadiene, was 92%.

COMPARATIVE EXAMPLE 4

Using the same apparatus as used in Example 3, a continuous operation of the reaction of 1,3-butadiene and water was carried out while recycling the catalyst. Upon expiration of 520 hours after initiation of the reaction, the state was as follows.

To the reactor 1, acetone as a recycling solvent (containing triethylamine), a recycling catalyst solution containing high boiling by-products, water and 1,3-butadiene were continuously supplied. The total amount of the feed supplied was 1,298 g/hr. The concentration of 1,3-butadiene and the total concentration of 1-hydroxy-2,7-octadiene and 3-hydroxy-1,7-octadiene in the total feed were 10.3 wt % and 1.7 wt %, respectively. The inner pressure of the autoclave was maintained at 10 kg/cm$^2$G. The reaction temperature was 75° C., and the residence time of the reaction solution was 4 hours. The composition of the liquid phase portion in the reactor was maintained to be 37.6 wt % of acetone, 7.8 wt % of water, 4.7 wt % of 1,3-butadiene, 6.5 wt % of 1-hydoxy-2,7-octadiene, 0.3 wt % of 3-hydroxy-1,7-octadiene, 6.9 wt % of triethylamine, 26.6 wt % of high boiling by-products, 0.044 wt % of palladium (formed from palladium acetate) and 1.1 wt % of tris(2,5-xylyl)phosphine. Here, the high boiling by-products included the dioctadienyl ether, $C_{16}$ unsaturated hydrocarbons, $C_9$ unsaturated carboxylic acids, octadienyl dodecatrienyl ether, etc.

The composition of the oil layer separated by an oilwater separator 5 was 18 wt % of 1-hydroxy-2,7-octadiene, 0.8 wt % of 3-hydroxy-1,7-octadiene, 75.2 wt % of high boiling by-products, 0.126 wt % of palladium, and 3.1 wt % of tris(2,5-xylyl)phosphine. This oil layer was supplied to a distillation column 4, and the supplied amount was 460 g/hr.

The distillation column 4 was operated under a pressure of 20 mmHg at an internal temperature of the bottom of 120° C. with the residence time of the bottoms at the bottom portion being from 0.3 to 1.3 hours, and the amount of the bottoms discharged was adjusted so that the concentration of high boiling by-products in the reactor would be 25 wt %. The amount of the discharged bottoms was 370 g/hr, which contained 90 wt % of high boiling byproducts, 0.16 wt % of palladium and 3.7 wt % of tris(2,5-xylyl)phosphine. The discharged liquid containing the high boiling by-products was returned as a recycling catalyst solution to the rector. Other conditions were the same as in Example 3.

The weight ratio of the high boiling by-products to the conjugated alkadiene (1,3-butadiene) and the alkadienols (1-hydroxy-2,7-octadiene and 3-hydroxy-1,7-octadiene) present in reaction solution in the reactor in this state, was 2.31. The conversion of 1,3-butadiene was 54%, and the selectivity, based on 1,3-butadiene, for the total of 1-hydroxy-2,7-octadiene and 3-hydroxy-, 1,7-octadiene, was 78%.

FIG. 1 is a flow chart showing the construction of the apparatus used in Examples 3 and 4 and Comparative Example 4, wherein reference numeral 1 indicates a reactor, numeral 2 a gas-liquid separator, numerals 3 and 4 distillation columns, numeral 5 an oil-water separator and numeral 6 a compressor.

As described in the foregoing, according to the present invention, it is possible to accomplish high selectivity for alkadienols while maintaining a high conversion of the conjugated alkadiene at a conjugated alkadiene concentration in the reaction solution being within a range of from 0.5 to 4.5 wt %, and the amount of an unreacted conjugated alkadiene discharged from the reaction solution is little, whereby the compressor for recycling the unreacted conjugated alkadiene to the reactor may be of a small size. Accordingly, the continuous method for producing alkadienols of the present invention is very advantageous from the industrial point of view.

What is claimed is::

1. A method for continuously producing alkadienols, which comprises subjecting a conjugated alkadiene and water to a hydration dimerization reaction in a continuous type reactor in the presence of carbon dioxide and a catalyst comprising a palladium compound and a phosphorus compound, wherein a hydrophobic phosphorus compound is used as the phosphorus compound, and the reaction is carried out in the presence of an amine while maintaining the concentration of the conjugated alkadiene in the reaction solution in the reactor within a range of from 0.5 to 4.5 wt %.

2. The continuous method according to claim 1, wherein the reaction is carried out under such a condition that the conversion of the conjugated alkadiene is at least 75%.

3. The continuous method according to claim 2, wherein the reaction is carried out under such a condition that the conversion of the conjugated alkadiene is at least 80%.

4. The continuous method according to claim 1, wherein the molar ratio of the water/the conjugated alkadiene in the reaction solution in the reactor is maintained at a level of at least 4.

5. The continuous method according to claim 1, wherein the concentration of the conjugated alkadiene in the reaction solution in the reactor is maintained within a range of from 0.5 to 4.0 wt %.

6. The continuous method according to claim 1, wherein the amount of the palladium compound in the reactor is from 0.00001 to 1 mol, as the amount of palladium atoms, per mol of the conjugated alkadiene.

7. The continuous method according to claim 1, wherein a phosphine or phosphite having at least 19 carbon atoms, is used as the hydrophobic phosphorus compound.

8. The continuous method according to claim 7, wherein the hydrophobic phosphorus compound is selected from the group consisting of tritolylphosphine, trixylylphosphine, trimesitylphosphine and tris(tetramethylphenyl)phosphine.

9. The continuous method according to claim 1, wherein the amine is a tertiary amine.

10. The continuous method according to claim 9, wherein the amine is a trialkylamine.

11. The continuous method according to claim 1, wherein a reaction product is recovered from the reaction solution containing the catalyst, withdrawn from the reactor, and at least a part of the catalyst is recycled to the reactor for reuse.

12. The continuous method according to claim 1, wherein the reaction is carried out while maintaining the ratio of the weight of high boiling by-products present in the reaction solution in the reactor to the total weight of the conjugated alkadiene and the alkadienols within a range of from 0.1 to 2.0.

13. The continuous method according to claim 1, wherein a reaction product is recovered from the reaction solution containing the catalyst, withdrawn from the reactor, and at least a part of the catalyst is recycled to the reactor for reuse, and wherein the reaction is carried out while maintaining the ratio of the weight of high boiling by-products present in the reaction solution in the reactor to the total weight of the conjugated alkadiene and the alkadienols within a range of from 0.1 to 2.0.

14. The continuous method according to claim 13, wherein the reaction is carried out while maintaining the ratio of the weight of high boiling by-products present in the reaction solution in the reactor to the total weight of the conjugated alkadiene and the alkadienols within a range of from 0.15 to 1.2.

15. The continuous method according to claim 1, wherein the hydration dimerization reaction is carried out at a reaction temperature of from 50° to 130° C. under a pressure of from 3 to 70 kg/cm² for a residence time of from 0.1 to 8 hours.

16. The continuous method according to claim 1, wherein the conjugated alkadiene is 1,3-butadiene.

* * * * *